United States Patent
Kondo

(10) Patent No.: US 11,408,873 B2
(45) Date of Patent: Aug. 9, 2022

(54) GAS SENSOR SYSTEM

(71) Applicant: NGK INSULATORS, LTD., Aichi (JP)

(72) Inventor: Yuichiro Kondo, Obu (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 17/213,755

(22) Filed: Mar. 26, 2021

(65) Prior Publication Data

US 2021/0302401 A1    Sep. 30, 2021

(30) Foreign Application Priority Data

Mar. 30, 2020   (JP) ............... JP2020-059366
Oct. 8, 2020    (JP) ............... JP2020-170621

(51) Int. Cl.
    *G01N 33/00*    (2006.01)
    *G01N 31/10*    (2006.01)
    *F01N 3/20*     (2006.01)

(52) U.S. Cl.
    CPC ....... *G01N 33/0037* (2013.01); *F01N 3/2066* (2013.01); *G01N 31/10* (2013.01); *F01N 2560/021* (2013.01); *F01N 2900/1621* (2013.01)

(58) Field of Classification Search
    CPC .......... G01N 33/0037; G01N 31/10; G01N 27/4075; G01N 27/407; F01N 3/2066; F01N 2560/021; F01N 2900/1621; F01N 11/00; F01N 2560/02; F01N 2560/026; Y02A 50/20; Y02T 10/40
    See application file for complete search history.

(56) References Cited

U.S. PATENT DOCUMENTS

2016/0356196 A1*  12/2016  Nakano ............ F01N 9/00

FOREIGN PATENT DOCUMENTS

JP    2001-133447 A    5/2001

* cited by examiner

*Primary Examiner* — Brandon D Lee
(74) *Attorney, Agent, or Firm* — Mattingly & Malur, PC

(57) ABSTRACT

A gas sensor system is equipped with a first gas detection unit, and a second gas detection unit. The first and second gas detection units include a gas introduction port for introducing a gas to be measured, a measurement chamber communicating with the gas introduction port, a conversion medium ($NH_3$ oxidation catalyst) arranged between the gas introduction port and the measurement chamber, and which converts a portion of a first gas type into a second gas type, and a detection device that detects the second gas type. A ratio of diffusion resistances of the first gas detection unit and the second gas detection unit is greater than or equal to 0.71 and less than or equal to 1.4.

4 Claims, 8 Drawing Sheets

FIG. 3

| SENSOR ELEMENT | R [mm$^{-1}$] | S(NO) [nA/ppm] | S(NH3) [nA/ppm] | Sr [-] |
|---|---|---|---|---|
| SENSOR Sa | 150 | 2.00 | 2.40 | 1.2 |
| SENSOR Sb | 220 | 1.36 | 1.64 | 1.2 |
| SENSOR Sc | 80 | 3.75 | 4.50 | 1.2 |
| SENSOR Sd | 80 | 3.75 | 3.75 | 1.0 |
| SENSOR Se | 115 | 2.61 | 2.35 | 0.9 |
| SENSOR Sf | 185 | 1.62 | 1.14 | 0.7 |
| SENSOR Sg | 220 | 1.36 | 0.82 | 0.6 |

FIG. 6

| | SENSOR ELEMENT | Ra [mm$^{-1}$] | SENSOR ELEMENT | Rb [mm$^{-1}$] | D [mm$^{-1}$] | P [-] | E [ppm] |
|---|---|---|---|---|---|---|---|
| EXEMPLARY EMBODIMENT 1 | SENSOR Sa | 150 | SENSOR Sd | 80 | 70 | 1.88 | 488 |
| EXEMPLARY EMBODIMENT 2 | SENSOR Sa | 150 | SENSOR Se | 115 | 35 | 1.30 | 157 |
| EXEMPLARY EMBODIMENT 3 | SENSOR Sa | 150 | SENSOR Sf | 185 | 35 | 1.23 | 148 |
| EXEMPLARY EMBODIMENT 4 | SENSOR Sa | 150 | SENSOR Sg | 220 | 70 | 1.47 | 337 |
| EXEMPLARY EMBODIMENT 5 | SENSOR Sb | 220 | SENSOR Sg | 220 | 0 | 1.00 | 51 |
| EXEMPLARY EMBODIMENT 6 | SENSOR Sc | 80 | SENSOR Sd | 80 | 0 | 1.00 | 14 |

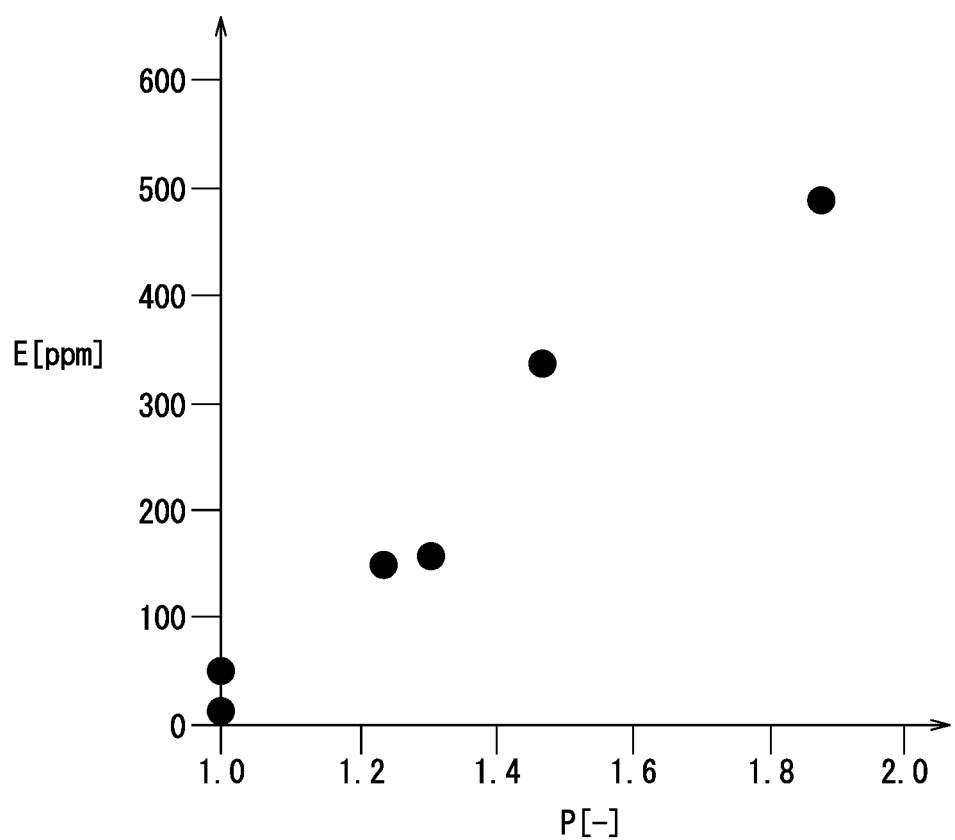

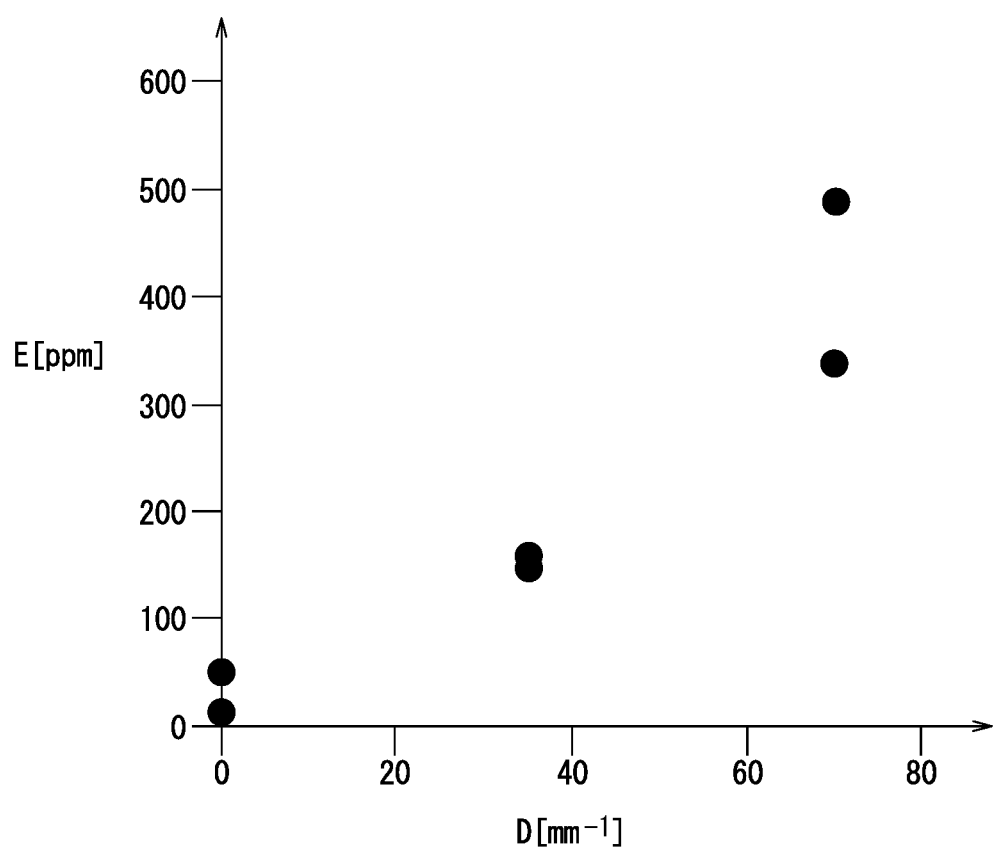

GAS SENSOR SYSTEM

CROSS-REFERENCE TO RELATED APPLICATIONS

This application is based upon and claims the benefit of priority from Japanese Patent Applications No. 2020-059366 filed on Mar. 30, 2020 and No. 2020-170621 filed on Oct. 8, 2020, the contents all of which are incorporated herein by reference.

BACKGROUND OF THE INVENTION

Field of the Invention

The present invention relates to a gas sensor system.

Description of the Related Art

Devices have been developed that are capable of measuring the concentrations of a plurality of gas types (e.g., NOx and $NH_3$). For example, Japanese Laid-Open Patent Publication No. 2001-133447 discloses the following device. In such a device, an amount of NOx and an amount of $NH_3$ within a gas to be measured are calculated from a total amount of NOx after having converted $NH_3$ within the gas to be measured (which includes NOx and $NH_3$) into NOx, and a total amount of NOx after having converted a portion of the $NH_3$ within the gas to be measured into NOx.

SUMMARY OF THE INVENTION

In this instance, the concentrations of the components of the gas may undergo a change over time. For example, in an exhaust gas from an automobile, concentrations of the components of the exhaust gas change accompanying a change in the operating state of the engine. In the case that the concentrations of the components of the gas change in this manner, it is not always easy to maintain the measurement accuracy.

An object of the present invention is to provide a gas sensor system which aims to improve measurement accuracy with respect to a mixed gas in which the concentrations of the components of the gas change over time.

The gas sensor system according to one aspect of the present invention is equipped with a first gas detection unit, a second gas detection unit, and a calculation unit. The first gas detection unit includes a first gas introduction port configured to introduce a gas to be measured containing at least one of a first gas type and a second gas type, a first measurement chamber in communication with the first gas introduction port, a first conversion medium disposed between the first gas introduction port and the first measurement chamber, and configured to convert a portion of the first gas type into the second gas type, and a first detection device configured to detect the second gas type in the first measurement chamber. The second gas detection unit includes a second gas introduction port configured to introduce the gas to be measured, a second measurement chamber in communication with the second gas introduction port, a second conversion medium disposed between the second gas introduction port and the second measurement chamber, and configured to convert a portion of the first gas type into the second gas type, and a second detection device configured to detect the second gas type in the second measurement chamber. The calculation unit is configured to calculate concentrations of the first gas type and the second gas type in the gas to be measured, based on detection results of the first detection device and the second detection device. The conversion efficiencies of the first conversion medium and the second conversion medium differ from each other. A ratio of a first diffusion resistance from the first gas introduction port to the first measurement chamber, and a second diffusion resistance from the second gas introduction port to the second measurement chamber is greater than or equal to 0.71 and less than or equal to 1.4.

According to the present invention, it is possible to provide a gas sensor system in which the measurement accuracy, with respect to a mixed gas in which the concentrations of the components of the gas change over time, is improved.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIG. 3 is a table showing characteristics of the sensor element which is used in an experiment;

FIG. 6 is a table showing experimental results;

FIG. 7 is a graph showing a relationship between diffusion resistance ratios and measurement errors; and FIG. 8 is a graph showing a relationship between differences in the diffusion resistance and the measurement errors.

DESCRIPTION OF THE PREFERRED EMBODIMENTS

A gas sensor system 10 according to an embodiment of the present invention will be presented and described in detail below.

Figure 1:
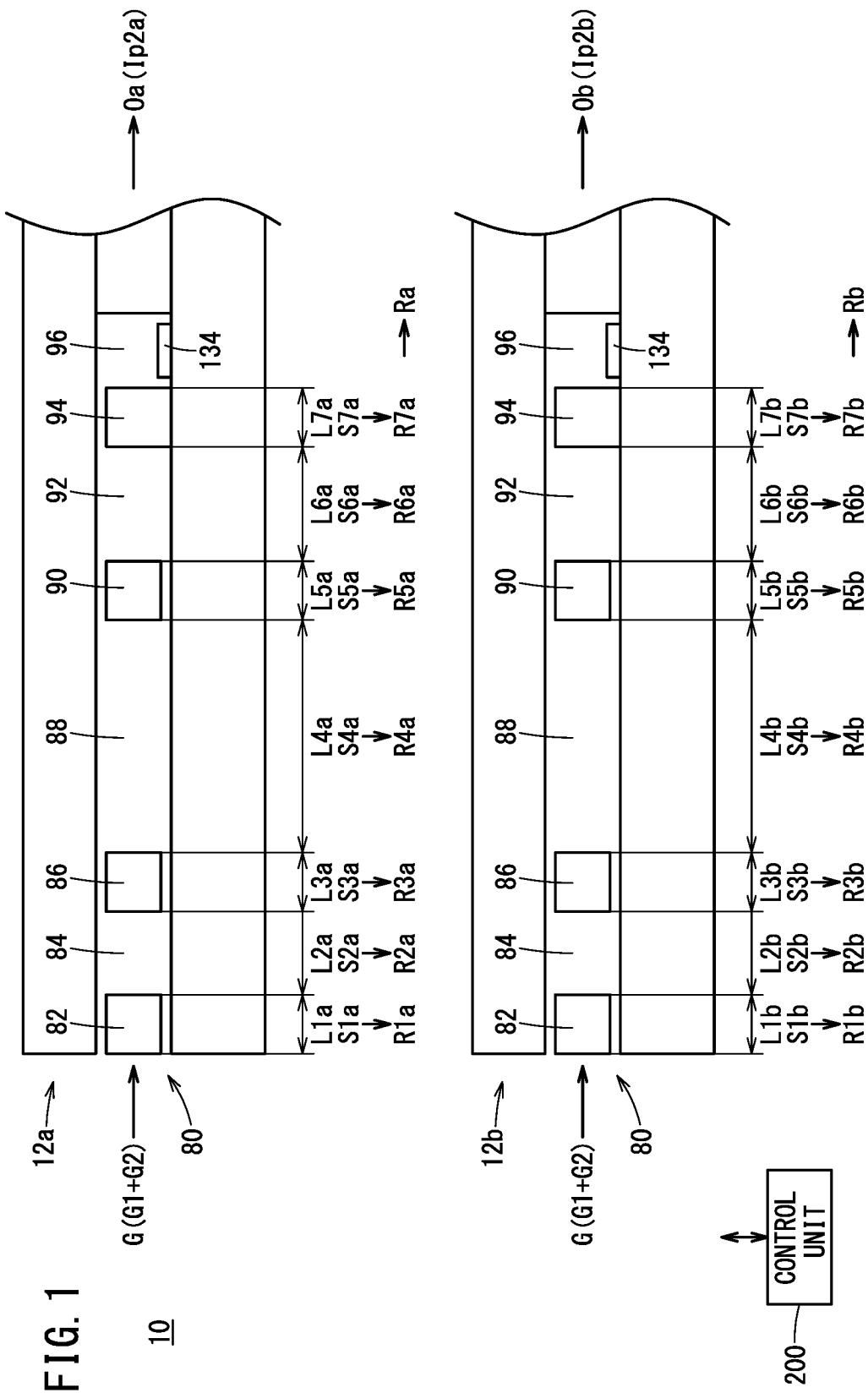
FIG. 1 is a diagram showing a gas sensor system according to an embodiment of the present invention.

FIG. 1 is a diagram showing the gas sensor system 10 according to an embodiment of the present invention. The gas sensor system 10 includes sensor elements 12a and 12b, and a control unit 200. In FIG. 1, in order to facilitate understanding, only portions of the sensor elements 12a and 12b are shown, and details thereof are omitted.

As shown in FIG. 1, each of the sensor elements 12a and 12b includes a gas introduction port 80, a first diffusion rate control member 82, a buffer space 84, a second diffusion rate control member 86, a first internal vacancy 88, a third diffusion rate control member 90, a second internal vacancy 92, a fourth diffusion rate control member 94, and a third internal vacancy 96 (measurement chamber). A gas to be measured G is introduced from the gas introduction ports 80, and reaches the third internal vacancy 96.

In this instance, the gas to be measured G includes at least one of a plurality of gas types G1 (for example, $NH_3$) and G2 (for example, NOx). The sensor elements 12a and 12b include a conversion medium (for example, a $NH_3$ oxidation catalyst), which oxidizes $NH_3$ and converts it into NOx, in at least one of the first diffusion rate control members 82, the buffer spaces 84, the second diffusion rate control members 86, the first internal vacancies 88, the third diffusion rate control members 90, the second internal vacancies 92, and the fourth diffusion rate control members 94.

The conversion mediums CM1 and CM2 of the sensor elements 12a and 12b possess different conversion efficiencies Ma and Mb. As a result, when the gas to be measured G reaches the third internal vacancies 96 (measurement chambers) of the sensor elements 12a and 12b, the concentrations of NOx, which are generated by oxidation of $NH_3$, differ from each other. Details concerning the conversion mediums CM1 and CM2 and the conversion efficiencies Ma and Mb will be described later.

The NOx that was originally present within the gas to be measured G after having reached the third internal vacancies 96, and the NOx which is newly generated by the oxidation of $NH_3$ in the gas to be measured G are detected using the detection devices (measurement pump cells 140, to be described later), and detected values Oa and Ob (Ip2a and Ip2b: pump currents Ip2, to be described later) corresponding to the sum of the concentrations of NOx are output. The detected values Oa and Ob exhibit a relationship, as represented by the following equations (1), for example, between the $NH_3$ concentration C1 and the NOx concentration C2 within the initial gas to be measured G. In this instance, Ka and Kb are proportionality constants representative of magnitudes of detected values with respect to the NOx concentrations of the sensor elements 12a and 12b, respectively.

$$Oa=Ka*(1.2*Ma*C1+C2)$$

$$Ob=Kb*(1.2*Mb*C1+C2) \quad (1)$$

From the detected values Oa and Ob, the control unit 200 calculates the $NH_3$ concentration C1 and the NOx concentration C2 within the initial gas to be measured G, for example, based on the following equations (2).

$$C1=(Oa/Ka-Ob/Kb)/(1.2*Ma-1.2*Mb)$$

$$C2=(-Mb*Oa/Ka+Ma*Ob/Kb)/(Ma-Mb) \quad (2)$$

Figure 2:
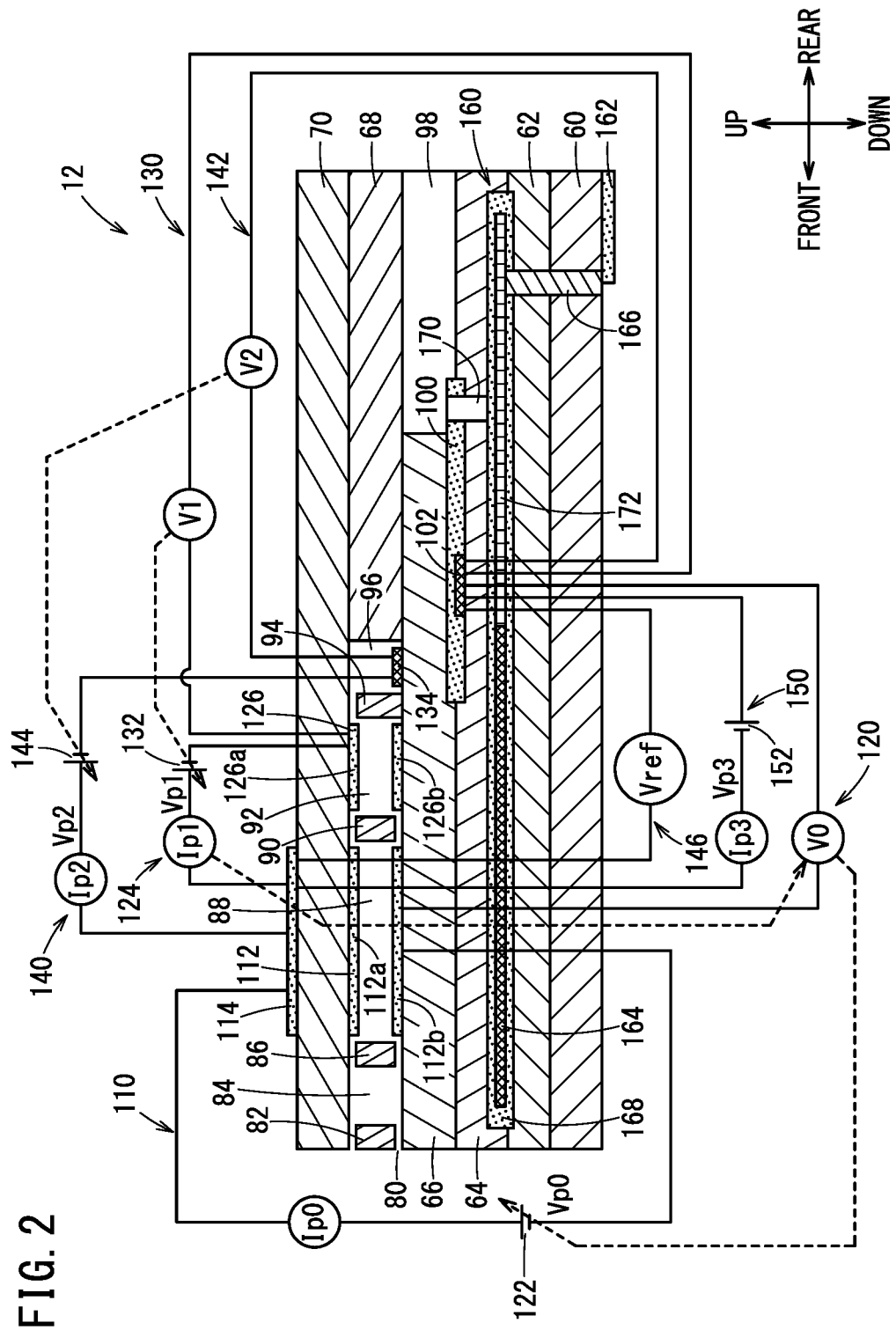
FIG. 2 is a cross-sectional view of a sensor element according to the embodiment.

Details concerning the sensor elements 12a and 12b will be described below. Since differences between the configurations of the sensor elements 12a and 12b are small, sensor elements 12 will be described together collectively, whereas points that differ between the sensor elements 12a and 12b will be added to the description in a supplemental manner. FIG. 2 is a cross-sectional view of the sensor elements 12 (12a and 12b) according to the embodiment.

The sensor elements 12 are of an elongate rectangular body shape, the longitudinal direction of the sensor elements 12 (the horizontal direction as shown in FIG. 2) is defined as a front-rear direction, and the thickness direction of the sensor elements 12 (the vertical direction as shown in FIG. 2) is defined as an up-down direction. Further, the widthwise direction of the sensor elements 12 (the direction perpendicular to the front-rear direction and the up-down direction) is defined as a left-right direction.

Each of the sensor elements 12 is an element including a laminated body in which six layers of a first substrate layer 60, a second substrate layer 62, a third substrate layer 64, a first solid electrolyte layer 66, a spacer layer 68, and a second solid electrolyte layer 70, made up respectively from an oxygen ion conductive solid electrolyte layer such a zirconia ($ZrO_2$) or the like, are stacked in this order from a lower side as viewed in the drawing. Further, the solid electrolyte that forms these six layers is dense and airtight. For example, after having performed a predetermined process such as printing of circuit patterns on ceramic green sheets corresponding to the respective layers, the sensor elements 12 are manufactured by laminating, and furthermore, firing and integrating the respective layers.

A gas introduction port 80, a first diffusion rate control member 82, a buffer space 84, a second diffusion rate control member 86, a first internal vacancy 88, a third diffusion rate control member 90, a second internal vacancy 92, a fourth diffusion rate control member 94, and a third internal vacancy 96 are formed adjacent to each other in this order, at one end of the sensor elements 12 (the left side in FIG. 2) between the lower surface of the second solid electrolyte layer 70 and the upper surface of the first solid electrolyte layer 66.

The gas introduction port 80, the buffer space 84, the first internal vacancy 88, the second internal vacancy 92, and the third internal vacancy 96 are spaces in the interior of the sensor elements 12, in which the upper portions thereof, which are provided by way of hollowing out the spacer layer 68, are defined by lower surfaces of the second solid electrolyte layer 70, the lower portions thereof are defined by upper surfaces of the first solid electrolyte layer 66, and the side portions thereof are defined by side surfaces of the spacer layer 68.

Any of the first diffusion rate control member 82, the second diffusion rate control member 86, and the third diffusion rate control member 90 is provided as two horizontally elongated slits (in which openings thereof have a longitudinal direction in a direction perpendicular to the drawing). Further, the fourth diffusion rate control member 94 is provided as a single horizontally elongated slit (in which the opening thereof has a longitudinal direction in a direction perpendicular to the drawing) formed as a gap between a lower surface of the second solid electrolyte layer 70. The portion from the gas introduction port 80 to the third internal vacancy 96 is also referred to as a gas to be measured flow through section.

Further, at a position more distant from one end side than the gas to be measured flow through section, and between the upper surface of the third substrate layer 64 and the lower surface of the spacer layer 68, a reference gas introduction space 98 is provided at a position where the side portions are defined by the side surfaces of the first solid electrolyte layer 66. For example, the atmospheric gas is introduced into the reference gas introduction space 98 as a reference gas when measurement of the NOx concentration is performed.

An atmospheric gas introduction layer 100 is a layer made of a ceramic such as porous alumina, and which is exposed to the reference gas introduction space 98. The reference gas is introduced into the atmospheric gas introduction layer 100 through the reference gas introduction space 98. Further, the atmospheric gas introduction layer 100 is formed in a manner so as to cover a reference electrode 102. The atmospheric gas introduction layer 100 introduces the reference gas to the reference electrode 102, while imparting a predetermined diffusion resistance with respect to the reference gas inside the reference gas introduction space 98. Further, the atmospheric gas introduction layer 100 is formed in a manner so as to be exposed to the reference gas introduction space 98 more so than the reference electrode 102, only on the rear end side (the right side shown in FIG. 2) of the sensor elements 12. Stated otherwise, the reference gas introduction space 98 is not formed up to a location directly above the reference electrode 102. However, the reference electrode 102 may also be formed directly below the reference gas introduction space 98 shown in FIG. 2.

The reference electrode 102 is an electrode formed in a condition so as to be sandwiched between the upper surface of the third substrate layer 64 and the first solid electrolyte layer 66, and as noted above, the atmospheric gas introduction layer 100 which is connected to the reference gas introduction space 98 is disposed around the periphery thereof. Moreover, the reference electrode 102 is formed directly on the upper surface of the third substrate layer 64, and a portion thereof other than the portion in contact with the upper surface of the third substrate layer 64 is covered by the atmospheric gas introduction layer 100. Further, as will be discussed later, using the reference electrode 102, it becomes possible to measure the oxygen concentration (oxygen partial pressure) inside the first internal vacancy 88, inside the second internal vacancy 92, and inside the third internal vacancy 96. The reference electrode 102 is formed as a porous cermet electrode (for example, a cermet electrode of Pt and $ZrO_2$).

In the gas to be measured flow through section, the gas introduction port 80 is a site that opens with respect to the external space, and the gas to be measured G is drawn into the sensor elements 12 from the external space through the gas introduction port 80. The first diffusion rate control member 82 is a location that imparts a predetermined diffusion resistance with respect to the gas to be measured G which is drawn in from the gas introduction port 80. The buffer space 84 is a space provided in order to guide the gas to be measured G that is introduced from the first diffusion rate control member 82 to the second diffusion rate control member 86.

The second diffusion rate control member 86 is a location that imparts a predetermined diffusion resistance with respect to the gas to be measured G which is drawn into the first internal vacancy 88 from the buffer space 84. When the gas to be measured G, which is introduced from the exterior of the sensor elements 12 to the interior of the first internal vacancy 88, due to pressure fluctuations of the gas to be measured G in the external space (pulsations in the exhaust pressure, in the case that the gas to be measured G is an exhaust gas of an automobile), the gas to be measured G, which is rapidly drawn into the sensor elements 12 from the gas introduction ports 80, is not introduced directly into the first internal vacancy 88, but rather, is introduced into the first internal vacancy 88 after such fluctuations in the concentration of the gas to be measured G are canceled by passing through the first diffusion rate control member 82, the buffer space 84, and the second diffusion rate control member 86.

Consequently, fluctuations in the concentration of the gas to be measured G that is introduced into the first internal vacancy 88 become almost negligible. The first internal vacancy 88 is provided as a space for adjusting the oxygen partial pressure within the gas to be measured G that is introduced through the second diffusion rate control member 86. The concerned oxygen partial pressure is adjusted by operation of a later-described main pump cell 110.

The main pump cell 110 is an electrochemical pump cell, which is constituted by an inner side pump electrode 112 disposed on the inner surface of the first internal vacancy 88, an outer side pump electrode 114 disposed in a region corresponding to the inner side pump electrode 112 within the upper surface of the second solid electrolyte layer 70 in a manner of being exposed to the external space, and the second solid electrolyte layer 70 which is sandwiched between the two pump electrodes.

The inner side pump electrode 112 spans over the upper and lower solid electrolyte layers (the second solid electrolyte layer 70 and the first solid electrolyte layer 66) that partition the first internal vacancy 88, and the spacer layer 68. More specifically, a ceiling electrode portion 112a of the inner side pump electrode 112 is formed on a lower surface of the second solid electrolyte layer 70, thereby forming a ceiling surface of the first internal vacancy 88, and further, a bottom electrode portion 112b is formed directly on an upper surface of the first solid electrolyte layer 66, thereby forming a bottom surface of the first internal vacancy 88, while in addition, so that the ceiling electrode portion 112a and the bottom electrode portion 112b are connected, a side electrode portions (not shown) are formed on side wall surfaces (inner surfaces) of the spacer layer 68 forming both side wall portions of the first internal vacancy 88, and are disposed as a structure in which a tunnel formation is formed at the location where the side electrode portion is disposed.

The inner side pump electrode 112 and the outer side pump electrode 114 are formed as porous cermet electrodes (for example, cermet electrodes of $ZrO_2$ and Pt containing 1% of Au). Moreover, the inner side pump electrode 112 which is in contact with the gas to be measured G is formed using a material that weakens the reduction capability with respect to the NOx component within the gas to be measured G.

In the main pump cell 110, a desired pump voltage Vp0 is applied between the inner side pump electrode 112 and the outer side pump electrode 114, and a pump current Ip0 is made to flow in a positive direction or a negative direction between the inner side pump electrode 112 and the outer side pump electrode 114, whereby the oxygen inside the first internal vacancy 88 can be pumped out to the external space, or the oxygen in the external space can be pumped into the first internal vacancy 88.

Further, in order to detect the oxygen concentration (oxygen partial pressure) within the atmosphere inside the first internal vacancy 88, an electrochemical sensor cell, and more specifically, an oxygen partial pressure detecting sensor cell 120 for controlling the main pump, is constituted by the inner side pump electrode 112, the second solid electrolyte layer 70, the spacer layer 68, the first solid electrolyte layer 66, and the reference electrode 102.

By measuring the electromagnetic force V0 in the oxygen partial pressure detecting sensor cell 120 for controlling the main pump, it becomes possible to comprehend and determine the oxygen concentration (oxygen partial pressure) inside the first internal vacancy 88. Furthermore, the pump current Ip0 is controlled by feedback-controlling the pump voltage Vp0 of a variable power supply 122 in a manner so that the electromotive force V0 becomes constant. Consequently, the oxygen concentration inside the first internal vacancy 88 can be maintained at a predetermined constant value.

The third diffusion rate control member 90 imparts a predetermined diffusion resistance to the gas to be measured G, the oxygen concentration (oxygen partial pressure) of which is controlled by operation of the main pump cell 110 in the first internal vacancy 88, and is a location that guides the gas to be measured G into the second internal vacancy 92.

The second internal vacancy 92 is provided as a space for further carrying out adjustment of the oxygen partial pressure by an auxiliary pump cell 124, with respect to the gas to be measured G which is introduced through the third diffusion rate control member 90, after the oxygen concentration (oxygen partial pressure) has been adjusted beforehand in the first internal vacancy 88. In accordance with this feature, the oxygen concentration inside the second internal vacancy 92 can be kept constant with high accuracy, and therefore, in the sensor elements 12, it becomes possible to measure the NOx concentration with high accuracy.

The above-described auxiliary pump cell 124 is an auxiliary electrochemical pump cell, which is constituted by an auxiliary pump electrode 126 provided on an inner surface of the second internal vacancy 92, the outer side pump electrode 114 (without being limited to the outer side pump electrode 114, any suitable pump electrode on the outer side of the sensor elements 12 is suitable), and the second solid electrolyte layer 70.

The auxiliary pump electrode 126 is arranged inside the second internal vacancy 92, in a structure having a tunnel formation similar to that of the inner side pump electrode 112 provided inside the first internal vacancy 88. Stated otherwise, a ceiling electrode portion 126a is formed with respect to the second solid electrolyte layer 70 that makes up a ceiling surface of the second internal vacancy 92, and further, a bottom electrode portion 126b is formed directly on an upper surface of the first solid electrolyte layer 66 that makes up a bottom surface of the second internal vacancy 92, while in addition, a tunnel shape structure is formed in which side electrode portions (not shown) connecting the ceiling electrode portion 126a and the bottom electrode portion 126b are formed respectively on both walls surfaces of the spacer layer 68 constituting the side walls of the second internal vacancy 92. Moreover, in the same manner as the inner side pump electrode 112, the auxiliary pump electrode 126 is also formed using a material that weakens the reduction capability with respect to the NOx component within the gas to be measured G.

In the auxiliary pump cell 124, by applying a desired voltage Vp1 between the auxiliary pump electrode 126 and the outer side pump electrode 114, it becomes possible to pump out oxygen within the atmosphere inside the second internal vacancy 92 into the external space, or alternatively, to pump in oxygen from the external space into the second internal vacancy 92.

Further, in order to control the oxygen partial pressure within the atmosphere inside the second internal vacancy 92, an electrochemical sensor cell, and more specifically, an oxygen partial pressure detecting sensor cell 130 for controlling the auxiliary pump, is constituted by the auxiliary pump electrode 126, the reference electrode 102, the second solid electrolyte layer 70, the spacer layer 68, and the first solid electrolyte layer 66.

Moreover, the auxiliary pump cell 124 carries out pumping by a variable power supply 132, the voltage of which is controlled based on the electromotive force V1 detected by the oxygen partial pressure detecting sensor cell 130 for controlling the auxiliary pump. Consequently, the oxygen partial pressure within the atmosphere inside the second internal vacancy 92 is controlled so as to become a low partial pressure that does not substantially influence the measurement of NOx.

Further, together therewith, a pump current Ip1 thereof is used so as to control the electromotive force V0 of the oxygen partial pressure detecting sensor cell 120 for controlling the main pump. More specifically, the pump current Ip1 is input as a control signal to the oxygen partial pressure detecting sensor cell 120 for controlling the main pump, and by controlling the electromotive force V0 thereof, the gradient of the oxygen partial pressure within the gas to be measured G, which is introduced from the third diffusion rate control member 90 into the second internal vacancy 92, is controlled to remain constant at all times. When used as a NOx sensor, by the actions of the main pump cell 110 and the auxiliary pump cell 124, the oxygen concentration in the second internal vacancy 92 is maintained at a constant value on the order of 0.001 [ppm].

The fourth diffusion rate control member 94 imparts a predetermined diffusion resistance to the gas to be measured G, the oxygen concentration (oxygen partial pressure) of which is controlled by operation of the auxiliary pump cell 124 in the second internal vacancy 92, and is a location that guides the gas to be measured G into the third internal vacancy 96. The fourth diffusion rate control member 94 fulfills a role of limiting the amount of NOx that flows into the third internal vacancy 96.

The third internal vacancy 96 is provided as a space (measurement chamber) for performing a process in relation to measurement of the nitrogen oxide (NOx) concentration within the gas to be measured G, with respect to the gas to be measured G which is introduced through the fourth diffusion rate control member 94, after the oxygen concentration (oxygen partial pressure) has been adjusted beforehand in the second internal vacancy 92. Measurement of the NOx concentration is primarily performed by operation of a measurement pump cell 140 in the third internal vacancy 96.

The measurement pump cell 140 performs measurement of the NOx concentration in the gas to be measured G in the interior of the third internal vacancy 96. The measurement pump cell 140 is an electrochemical pump cell constituted by a measurement electrode 134, which is disposed directly on the upper surface of the first solid electrolyte layer 66 facing toward the third internal vacancy 96, the outer side pump electrode 114, the second solid electrolyte layer 70, the spacer layer 68, and the first solid electrolyte layer 66. The measurement electrode 134, for example, is a porous cermet electrode. The measurement electrode 134 also functions as a NOx reduction catalyst for reducing NOx existing within the atmosphere inside the third internal vacancy 96.

In the measurement pump cell 140, it is possible to pump out oxygen that is generated by the decomposition of nitrogen oxide within the atmosphere around the periphery of the measurement electrode 134, and to detect the generated amount as a pump current Ip2.

Further, in order to detect the oxygen partial pressure around the periphery of the measurement electrode 134, an electrochemical sensor cell, and more specifically, an oxygen partial pressure detecting sensor cell 142 for controlling the measurement pump, is constituted by the first solid electrolyte layer 66, the measurement electrode 134, and the reference electrode 102. A variable power supply 144 is controlled based on the electromotive force V2 detected by the oxygen partial pressure detecting sensor cell 142 for controlling the measurement pump.

The gas to be measured G which is guided into the second internal vacancy 92 reaches the measurement electrode 134 of the third internal vacancy 96 through the fourth diffusion rate control member 94 under a condition in which the oxygen partial pressure is controlled. Nitrogen oxide existing within the gas to be measured G around the periphery of the measurement electrode 134 is reduced ($2NO \rightarrow N_2 + O_2$) to thereby generate oxygen. In addition, although such generated oxygen is subjected to pumping by the measurement pump cell 140, the voltage Vp2 of the variable power supply 144 is controlled in a manner so that the electromotive force V2 detected by the oxygen partial pressure detecting sensor cell 142 for controlling the measurement pump becomes constant. Since the amount of oxygen generated around the periphery of the measurement electrode 134 is proportional to the concentration of nitrogen oxide within the gas to be measured G, the nitrogen oxide concentration within the gas to be measured G can be calculated using the pump current Ip2 of the measurement pump cell 140.

Further, an electrochemical sensor cell 146 is constituted by the second solid electrolyte layer 70, the spacer layer 68, the first solid electrolyte layer 66, the third substrate layer 64, the outer side pump electrode 114, and the reference electrode 102, and in accordance with an electromotive force Vref obtained by the sensor cell 146, it is possible to detect the oxygen partial pressure within the gas to be measured G existing externally of the sensor.

Furthermore, an electrochemical reference gas adjusting pump cell 150 is constituted by the second solid electrolyte layer 70, the spacer layer 68, the first solid electrolyte layer 66, the third substrate layer 64, the outer side pump electrode 114, and the reference electrode 102. The reference gas adjusting pump cell 150 carries out pumping by distributing a control current Ip3 due to a voltage Vp3 applied by a variable power supply 152, which is connected between the outer side pump electrode 114 and the reference electrode 102. Consequently, the reference gas adjusting pump cell 150 draws in oxygen from the space around the periphery of the outer side pump electrode 114 into the space around the periphery of the reference electrode 102 (the atmospheric gas introduction layer 100). The voltage Vp3 of the variable power supply 152 is determined beforehand as a DC voltage, in a manner so that the control current Ip3 becomes a predetermined value (a DC current of a constant value).

In the sensor elements 12 having such a configuration, by operating the main pump cell 110 and the auxiliary pump cell 124, the gas to be measured G, in which the oxygen partial pressure thereof is always maintained at a constant low value (a value that does not substantially exert an influence on the measurement of NOx), is imparted to the measurement pump cell 140. Accordingly, it becomes possible for the NOx concentration within the gas to be measured G to be known, on the basis of the aforementioned pump current Ip2, which is distributed by pumping out the oxygen generated by the reduction of NOx from the measurement pump cell 140, substantially in proportion to the concentration of NOx within the gas to be measured G.

Furthermore, each of the sensor elements 12 is equipped with a heater unit 160 which plays a role in adjusting the temperature for heating, and to maintain the sensor elements 12 in a heated condition, for the purpose of increasing the oxygen ion conductivity of the solid electrolyte. The heater unit 160 comprises a heater connector electrode 162, a heater 164, a through hole 166, a heater insulating layer 168, a pressure dissipation hole 170, and a lead wire 172.

The heater connector electrode 162 is an electrode which is formed so as to be in contact with the lower surface of the first substrate layer 60. By the heater connector electrode 162 being connected to an external power supply, it becomes possible for power to be supplied from the exterior to the heater unit 160.

The heater 164 is an electric resistor formed in a state of being sandwiched from above and below between the second substrate layer 62 and the third substrate layer 64. The heater 164 is connected to the heater connector electrode 162 via a lead wire 172 and a through hole 166, generates heat by being supplied with electrical power from the exterior through the heater connector electrode 162, and carries out heating and maintains the heat of the solid electrolyte that forms the sensor elements 12.

Further, the heater 164 is embedded over the entire region from the first internal vacancy 88 to the third internal vacancy 96, whereby the sensor elements 12 as a whole are made capable of being adjusted to a temperature at which the solid electrolyte is activated.

The heater insulating layer 168 is an insulating layer made of porous alumina formed by an insulator of alumina or the like on the upper and lower surfaces of the heater 164. The heater insulating layer 168 is formed with the aim of obtaining electrical insulation between the second substrate layer 62 and the heater 164, as well as electrical insulation between the third substrate layer 64 and the heater 164.

The pressure dissipation hole 170 is a site that is provided so as to penetrate through the third substrate layer 64 and communicate with the reference gas introduction space 98, and is formed with the aim of alleviating an increase in internal pressure accompanying a rise in the temperature inside the heater insulating layer 168.

As discussed previously, in the present embodiment, a conversion medium (for example, a $NH_3$ oxidation catalyst) is included, which oxidizes $NH_3$ and converts it into NOx, in at least one of the first diffusion rate control members 82, the buffer spaces 84, the second diffusion rate control members 86, the first internal vacancies 88, the third diffusion rate control members 90, the second internal vacancies 92, and the fourth diffusion rate control members 94. For example, all or a portion of the first diffusion rate control members 82, the second diffusion rate control members 86, the third diffusion rate control members 90, and the fourth diffusion rate control members 94 can be configured by the $NH_3$ oxidation catalyst. Further, the $NH_3$ oxidation catalyst can be disposed in at least one of the buffer spaces 84, the first internal vacancies 88, and the second internal vacancies 92. Prior to reaching the third internal vacancies 96, the gas to be measured G passes through, for example, a layer of the $NH_3$ oxidation catalyst, and at least a portion of the $NH_3$ is changed into NOx.

As discussed previously, the conversion mediums CM1 and CM2 of the sensor elements 12a and 12b possess different conversion efficiencies Ma and Mb. As a combination of the conversion mediums CM1 and CM2, for example, a strong $NH_3$ oxidation catalyst having a conversion efficiency M which is close to 100%, and a weak $NH_3$ oxidation catalyst having a conversion efficiency M of 5 to 80% can be used. The strong $NH_3$ oxidation catalyst contains, for example, at least one component selected from among Pt, Au, Ag, Rh, and Pd. More specifically, the strong $NH_3$ oxidation catalyst contains at least one type of component selected from among Pt and Au, in which the composition ratio Au/(Pt+Au) is less than or equal to 1%. The weak $NH_3$ oxidation catalyst contains, for example, at least one component from among V, Mo, W, Fe, Co, Ni, Cu, Ag, Au, Rh, Pd, Cr, Pt, $V_2O_5$, $WO_3$, $TiO_2$, and $Al_2O_3$. More specifically, the weak $NH_3$ oxidation catalyst contains both the components of Pt and Au, and the composition ratio Au/(Pt+Au) is greater than or equal to 4% and less than or equal to 20%. In the strong $NH_3$ oxidation catalyst and the weak $NH_3$ oxidation catalyst, such components are supported on a porous ceramic body, or make up a porous cermet.

Moreover, instead of the $NH_3$ oxidation catalyst or in addition to the $NH_3$ oxidation catalyst, as the conversion mediums thereof, the inner side pump electrode 112 and the auxiliary pump electrode 126 may be made to possess a function of oxidizing $NH_3$.

In the present embodiment, the diffusion resistances R (Ra and Rb) applied to the gas to be measured G from the gas introduction ports 80 to the third internal vacancies 96 becomes a problem. As shown in FIG. 1 as well as in the following equation (3), the diffusion resistances R (Ra and Rb) are of the same partial diffusion resistances R1 to R7 (R1a to R7a and R1b to R7b) in each of the respective paths (the first diffusion rate control members 82, the buffer spaces 84, the second diffusion rate control members 86, the first internal vacancies 88, the third diffusion rate control members 90, the second internal vacancies 92, and the fourth diffusion rate control members 94).

$$Ra = R1a + R2a + \ldots + R7a = \sum_{i=1}^{7}(Ria) \quad (3)$$

$$Rb = R1b + R2b + \ldots + R7b = \sum_{i=1}^{7}(Rib)$$

As shown in equation (4), the partial diffusion resistances Ri are values obtained by dividing a path length Li by a cross-sectional area Si of each of the diffusion paths.

$$Ri = Li/Si \quad (4)$$

Accordingly, the diffusion resistances R (Ra and Rb) are defined by the following Equation (5).

$$Ra = \sum_{i=1}^{7}(Ria) \quad (5)$$
$$= \sum_{i=1}^{7}\left(\frac{Lia}{Sia}\right)$$
$$= \frac{L1a}{S1a} + \frac{L2a}{S2a} + \ldots + \frac{L7a}{S7a}$$

$$Rb = \frac{L1b}{S1b} + \frac{L2b}{S2b} + \ldots + \frac{L7b}{S7b}$$

Moreover, the partial diffusion resistances R1 to R7 in each of the paths are obtained while taking into consideration an influence due to providing the conversion medium.

The diffusion resistances R exert an influence on the responsiveness of the sensor elements 12. More specifically, as the diffusion resistances R become larger, more time is required from the gas introduction port 80 to the third internal vacancies 96, and a delay is generated in the responsiveness of the detected values O (Ip2) with respect to changes in the concentrations of the components of the gas to be measured G in the gas introduction port 80.

According to the present embodiment, from the fact that the detected values Oa and Ob from the plurality of sensor elements 12a and 12b are calculated, a deviation in the responsiveness of the sensor elements 12a and 12b results in a measurement error. More specifically, by the diffusion resistances Ra and Rb of the sensor elements 12a and 12b being brought into closer proximity to each other, the measurement accuracy of the $NH_3$ concentration C1 and the NOx concentration C2 in a dynamic atmosphere (in which the concentrations of the components of the gas to be measured G change over time) can be improved.

Next, as shown in the exemplary embodiments, a ratio of the diffusion resistances R (Ra and Rb) of the sensor elements 12a and 12b (diffusion resistance ratio P=Ra/Rb) is preferably greater than or equal to 0.71 and less than or equal to 1.4. Further, it is preferable for the absolute value of the difference between the diffusion resistances R (Ra and Rb) of the sensor elements 12a and 12b (difference between the diffusion resistances D=|Ra−Rb|) to be less than or equal to 40 [mm$^{-1}$].

Exemplary Embodiments

Hereinafter, exemplary embodiments will be described. FIG. 3 is a table showing characteristics of the sensor elements 12 which are used in an experiment. Sensors Sa to Sg were used as the sensor elements 12. The diffusion resistances R [mm$^{-1}$], the NOx sensitivity S(NO), the $NH_3$ sensitivity S($NH_3$), and the sensitivity ratios Sr of the sensors Sa to Sg are shown.

As discussed previously, the diffusion resistances R are diffusion resistances received by the gas to be measured G from the gas introduction port 80 to the third internal vacancy 96. In this instance, the NOx sensitivity S(NO) and the $NH_3$ sensitivity S($NH_3$) are proportionality constants [nA/ppm] representative of magnitudes of the pump currents Ip2 with respect to the NOx concentration C2 [ppm] and the $NH_3$ concentration C1 [ppm], respectively.

The sensitivity ratio Sr is representative of the magnitude of the $NH_3$ sensitivity S($NH_3$) with respect to the NOx sensitivity S(NO) in each of the sensors (Sr=S($NH_3$)/S(NO)). The sensitivity ratio Sr exhibits a relationship with the conversion efficiency M as shown, for example, in the following equation (6).

$$Sr = 1.2 * M \quad (6)$$

More specifically, by combining the sensor elements 12, the sensitivity ratios Sr of which differ from each other (the conversion efficiencies M thereof are different), it becomes possible to measure the $NH_3$ concentration C1 and the NOx concentration C2.

The diffusion resistances R of the sensors Sa to Sg were 150, 220, 80, 80, 115, 185, and 220 [mm$^{-1}$], respectively. The NOx sensitivities S(NO) of the sensors Sa to Sg were 2.00, 1.36, 3.75, 3.75, 2.61, 1.62, and 1.36 [nA/ppm], respectively. The $NH_3$ sensitivities S($NH_3$) of the sensors Sa to Sg were 2.40, 1.64, 4.50, 3.75, 2.35, 1.14, and 0.82 [nA/ppm], respectively. The sensitivity ratios Sr of the sensors Sa to Sg were 1.2, 1.2, 1.2, 1.0, 0.9, 0.7, and 0.6, respectively.

In this instance, using the gas to be measured G containing NOx but not containing $NH_3$, the concentration of the gas to be measured G was made to rapidly changed, and a measurement was performed thereon by the gas sensor system 10. More specifically, the initial concentration of NOx was 0 [ppm], and after 30 seconds, the concentration was increased to 500 [ppm] at a rate of change of 500 [ppm/s]. Such a state was continued for 15 seconds, and thereafter, the concentration was returned to 0 [ppm] at a rate of change of −500 [ppm/s]. The conditions for the gas to be measured at the time of measurement were a temperature of 250° C., a flow rate of 200 SLM (standard liter/min), and the gas components apart from NOx were 10% $O_2$+3% $H_2O$+$N_2$.

Figure 4:
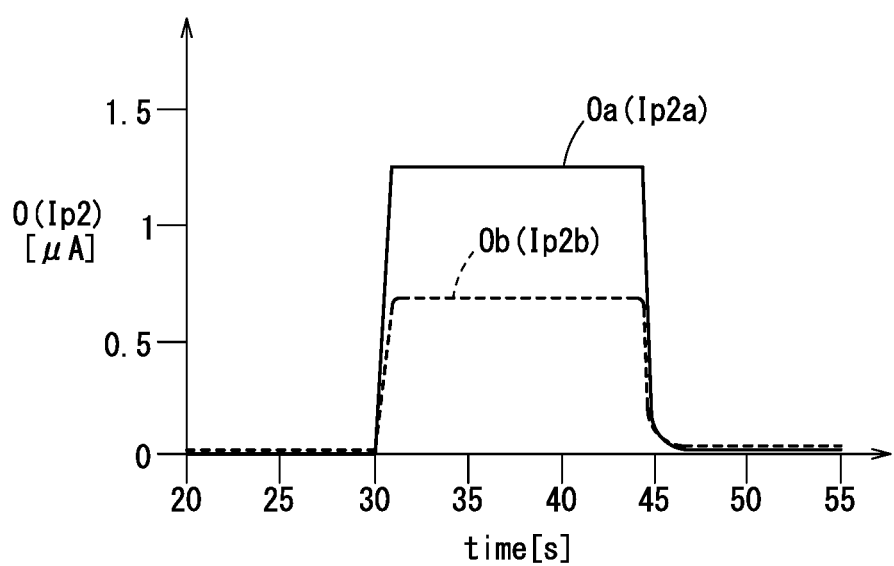
FIG. 4 is a graph showing changes over time of values detected by the sensor element.

FIG. 4 is a graph showing changes over time of the values Oa and Ob (pump currents Ip2) detected by the sensor elements 12a and 12b. At times of 30 seconds and 45 seconds, the pump current Ip2 changes abruptly.

Figure 5:
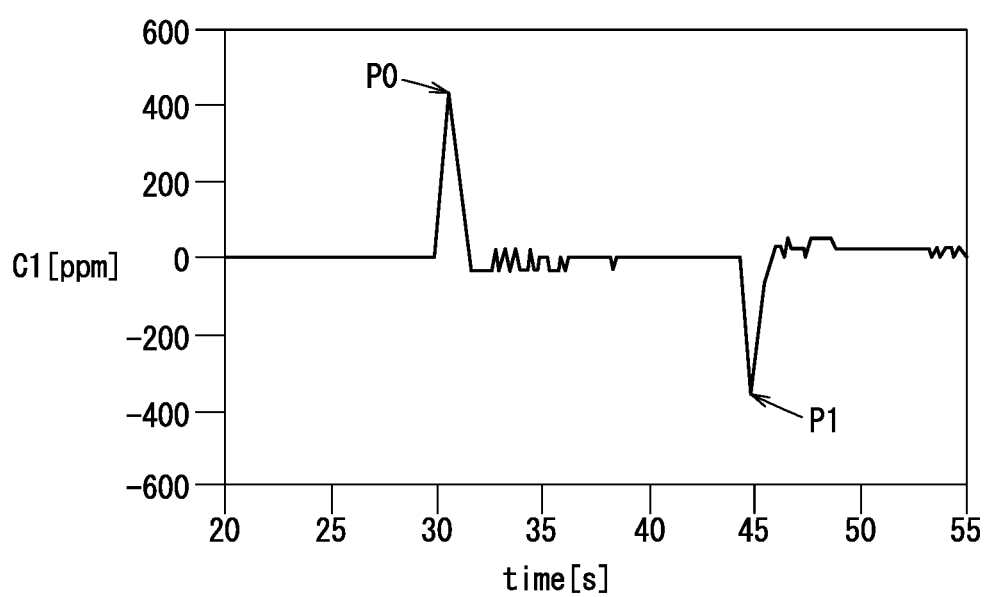
FIG. 5 is a graph showing changes over time of a calculated $NH_3$ concentration.

FIG. 5 shows the $NH_3$ concentration C1 that was calculated based on Equation (2) from the detected values Oa and Ob of the sensor elements 12a and 12b. In the vicinity of 30 seconds and 45 seconds, positive and negative peaks P0 and P1 are generated in the $NH_3$ concentration C1, notwithstanding the fact that the gas to be measured G does not contain NH$_3$. In particular, when the NOx concentration of the gas to be measured G changes abruptly, the detection accuracy of NH$_3$ is lowered. More specifically, the magnitudes of the peaks P0 and P1 can be placed as measurement errors E [ppm] of the NH$_3$ concentration C1.

FIG. 6 is a table showing experimental results. FIGS. 7 and 8 are graphs showing relationships between diffusion resistance ratios P, differences in the diffusion resistance D, and measurement errors E.

As shown in FIG. 6, tests were conducted on six combinations of Exemplary Embodiment 1 (sensors Sa and Sd), Exemplary Embodiment 2 (sensors Sa and Se), Exemplary Embodiment 3 (Sensors Sa and Sf), Exemplary Embodiment 4 (Sensors Sa and Sg), Exemplary Embodiment 5 (sensors Sb and Sg), and Exemplary Embodiment 6 (sensors Sc and Sd) having different sensitivity ratios Sr. The diffusion resistance ratios P of Exemplary Embodiments 1 to 6 were 1.88, 1.30, 1.23, 1.47, 1.00, and 1.00 [–], the differences in the diffusion resistance D thereof were 70, 35, 35, 70, 0, and 0 [mm$^{-1}$], and the measurement errors E thereof were 488, 157, 148, 337, 51, and 14 [ppm]. Moreover, the diffusion resistance ratios P were obtained by dividing the larger one of the diffusion resistances Ra and Rb by the smaller one (If both are equal, P=1).

As shown in FIGS. 7 and 8, the diffusion resistance ratios P and the differences in the diffusion resistance D have a close relationship with the measurement errors E. In order to suppress the measurement error E to remain less than or equal to 200 [ppm], the diffusion resistance ratio P is preferably greater than or equal to 1.0 and less than or equal to 1.4 (more preferably, less than or equal to 1.3). Taking into consideration a magnitude relationship between the diffusion resistances Ra and Rb, the diffusion resistance P is preferably greater than or equal to 0.71 (=1/1.4) and less than or equal to 1.4, and more preferably, is greater than or equal to 0.77 (=1/1.3) and less than or equal to 1.3. Further, the difference in the diffusion resistance D is preferably less than or equal to 40 [mm$^{-1}$] (more preferably, less than or equal to 30 [mm$^{-1}$]).

As described above, according to the present embodiment, the gas sensor system 10 can be configured in which, by setting the ratio of the diffusion resistances Ra and Rb (diffusion resistance ratio P) of the sensor elements 12a and 12b to be greater than or equal to 0.71 and less than or equal to 1.4, the measurement error E in the case that the concentrations change over time is reduced.

In the foregoing configuration, separate sensor elements 12a and 12b are used, however, the sensor elements 12a and 12b may be configured in an integrated fashion. For example, utilizing a structure made up from an oxygen ion conductive solid electrolyte or the like, a first gas detection unit and a second gas detection unit may be configured having functions corresponding to the sensor elements 12a and 12b.

Technical Concepts Obtained from the Embodiment

A description will be given below concerning technical concepts that can be grasped from the above-described embodiment.

[1] The gas sensor system (10) is equipped with the first gas detection unit (the sensor element 12a), the second gas detection unit (the sensor element 12b), and the calculation unit (control unit 200). The first gas detection unit includes a first gas introduction port 80 configured to introduce a gas to be measured (G) containing at least one of a first gas type (gas type G1) and a second gas type (gas type G2), a first measurement chamber (third internal vacancy 96) in communication with the first gas introduction port, a first conversion medium (NH$_3$ oxidation catalyst, CM1) disposed between the first gas introduction port and the first measurement chamber, and configured to convert a portion of the first gas type into the second gas type, and a first detection device (measurement pump cell 140) configured to detect the second gas type in the first measurement chamber. The second gas detection unit includes a second gas introduction port 80 configured to introduce the gas to be measured (G), a second measurement chamber (third internal vacancy 96) in communication with the second gas introduction port, a second conversion medium (NH$_3$ oxidation catalyst, CM2) disposed between the second gas introduction port and the second measurement chamber, and configured to convert a portion of the first gas type into the second gas type, and a second detection device (measurement pump cell 140) configured to detect the second gas type in the second measurement chamber. The calculation unit is configured to calculate the concentrations of the first gas type and the second gas type in the gas to be measured, based on detection results of the first detection device and the second detection device. The conversion efficiencies of the first conversion medium and the second conversion medium differ from each other. A ratio (diffusion resistance ratio P) of the first diffusion resistance (Ra) from the first gas introduction port to the first measurement chamber, and the second diffusion resistance (Rb) from the second gas introduction port to the second measurement chamber is greater than or equal to 0.71 and less than or equal to 1.4. In accordance with such a configuration, with the diffusion resistance ratio P being greater than or equal to 0.71 and less than or equal to 1.4, the measurement accuracy of the gas when the concentrations of the components of the gas change over time can be improved.

[2] The absolute value of the difference between the first diffusion resistance and the second diffusion resistance (difference in the diffusion resistance D) is less than or equal to 40 [mm$^{-1}$]. In accordance with this feature, the measurement accuracy of the gas when the concentrations of the components of the gas change over time can be further improved.

[3] The first gas detection unit and the second gas detection unit are integrally formed by a structural body made up from an oxygen ion conductive solid electrolyte. In accordance with this feature, the first gas detection unit and the second gas detection unit can be configured in an integrated fashion, and the gas sensor system can be made compact.

[4] The first gas type is NH$_3$, and the second gas type is NOx. In accordance with this feature, the measurement accuracy when the concentration of NH$_3$ or NOx changes over time can be further improved.

The present invention is not particularly limited to the embodiment described above, and various modifications are possible without departing from the essence and gist of the present invention.

What is claimed is:

1. A gas sensor system, comprising:
    a first gas introduction port configured to introduce a gas to be measured containing at least one of a first gas type and a second gas type;
    a first measurement chamber in communication with the first gas introduction port;
    a first conversion medium disposed between the first gas introduction port and the first measurement chamber, and configured to convert a portion of the first gas type into the second gas type;

a first gas detection unit including a first detection device configured to detect the second gas type in the first measurement chamber;

a second gas introduction port configured to introduce the gas to be measured;

a second measurement chamber in communication with the second gas introduction port;

a second conversion medium disposed between the second gas introduction port and the second measurement chamber, and configured to convert a portion of the first gas type into the second gas type;

a second gas detection unit including a second detection device configured to detect the second gas type in the second measurement chamber; and a calculation unit configured to calculate concentrations of the first gas type and the second gas type in the gas to be measured, based on detection results of the first detection device and the second detection device;

wherein conversion efficiencies of the first conversion medium and the second conversion medium differ from each other; and a ratio of a first diffusion resistance from the first gas introduction port to the first measurement chamber, and a second diffusion resistance from the second gas introduction port to the second measurement chamber is greater than or equal to 0.71 and less than or equal to 1.4.

2. The gas sensor system according to claim 1, wherein an absolute value of a difference between the first diffusion resistance and the second diffusion resistance is less than or equal to 40 [mm$^{-1}$].

3. The gas sensor system according to claim 1, wherein the first gas detection unit and the second gas detection unit are integrally formed by a structural body made up from an oxygen ion conductive solid electrolyte.

4. The gas sensor system according to claim 1, wherein the first gas type is $NH_3$, and the second gas type is NOx.

* * * * *